(12) United States Patent
Gerard et al.

(10) Patent No.: US 8,224,047 B2
(45) Date of Patent: Jul. 17, 2012

(54) SYSTEM AND METHOD FOR MEASURING LEFT VENTRICULAR TORSION

(75) Inventors: Olivier Gerard, Viroflay (FR); Pascal Allain, Versailles (FR); Heinrich Beckermann, Herrenberg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 1054 days.

(21) Appl. No.: 12/065,589

(22) PCT Filed: Sep. 1, 2006

(86) PCT No.: PCT/IB2006/053068
§ 371 (c)(1),
(2), (4) Date: Mar. 3, 2008

(87) PCT Pub. No.: WO2008/026022
PCT Pub. Date: Mar. 6, 2008

(65) Prior Publication Data
US 2008/0199064 A1    Aug. 21, 2008

(51) Int. Cl.
*G06K 9/00* (2006.01)
*G06K 9/62* (2006.01)
*A61B 8/00* (2006.01)
(52) U.S. Cl. .................. 382/128; 382/216; 600/450
(58) Field of Classification Search .............. 382/128
See application file for complete search history.

(56) References Cited

U.S. PATENT DOCUMENTS

| 6,289,135 | B1 * | 9/2001 | Declerck et al. | 382/276 |
|---|---|---|---|---|
| 6,535,570 | B2 * | 3/2003 | Stergiopoulos et al. | 378/8 |
| 6,873,866 | B2 | 3/2005 | Briandet | |
| 7,526,113 | B2 * | 4/2009 | Jacob et al. | 382/128 |
| 2002/0072670 | A1 * | 6/2002 | Chenal et al. | 600/449 |
| 2004/0125997 | A1 | 7/2004 | Jacob | |
| 2005/0085729 | A1 * | 4/2005 | Abe | 600/450 |
| 2005/0111717 | A1 * | 5/2005 | Yoshioka et al. | 382/128 |

OTHER PUBLICATIONS

Notomi et al., Measurement of Ventricular Torsion by Two-Dimensional Ultrasound Speckle Tracking Imaging, Journal of the American College of Cardiology, vol. 45, No. 12, Jun. 21, 2005, pp. 2034-2041.*

(Continued)

*Primary Examiner* — David Zarka
(74) *Attorney, Agent, or Firm* — W. Brinton Yorks, Jr.

(57) ABSTRACT

A system and method are provided for determining at least one torsion angle of a left ventricle. The method includes the steps of collecting three-dimensional ultrasound data of the left ventricle (36) to obtain at least one first two-dimensional view and at least one second two-dimensional view thereof, wherein the first two-dimensional view is obtained at about the beginning of a cardiac phase and the second two-dimensional view is obtained at about the end of the cardiac phase, placing at least two tracking points (40, 42) on the at least one first two-dimensional view to draw a first torsion line (44), tracking the at least two tracking points to extrapolate the position thereof on the at least one second two-dimensional view and to draw a second torsion line (46), and calculating the at least one torsion angle by measuring an angle (A) formed by the intersection of the first and second torsion lines (44, 46).

22 Claims, 7 Drawing Sheets

OTHER PUBLICATIONS

Helle-Valle et al., New Noninvasive Method for Assessment of Left Ventricular Rotation, Circulation, Journal of the American Heart Association, vol. 112, pp. 3149-3156, Nov. 15, 2005.*

Dong et al., Independent effects of preload, afterload, and contractility on left ventricular torsion, AJP, Heart and Circulatory Physiology, vol. 277, pp. H1053-H1060, 1999.*

Notomi, Y. et al "Measurement of Ventricular Torsion by Two-Dimensional Ultrasound Speckle Tracking Imaging", Journal of the American College of Cardiology, vol. 45, No. 12, 2005.

Lamberti, C. et al Topology of Optical Flow in 3d Echocardiography Computers in Cardiology vol. 24, 1997.

* cited by examiner

FIG. 11

SYSTEM AND METHOD FOR MEASURING LEFT VENTRICULAR TORSION

The present disclosure relates generally to ultrasound image quantification and more specifically to a system and method for measuring left ventricular torsion using three-dimensional ultrasound data.

Left ventricular (LV) torsion or twist is counterclockwise rotation of the ventricular apex with respect to the base during systole. More particularly, LV torsion is a rotation of about 10° around the LV axis. Until recently it has been thought that LV torsion is of little clinical relevance. Lately, that view has changed and it is believed that measuring LV torsion can be valuable in diagnosing certain cardiovascular diseases, such as ischemic disease—a condition in which blood flow is restricted to portions of the body.

Attempts have been made to measure LV torsion using complicated cineradiography techniques where a piece of radiopaque wire (e.g., stainless steel) was implanted into cardiac tissue as a reference line. Other less invasive techniques have also been used to study LV torsion, such as magnetic resonance imaging (MRI) and transesophagal echocardiogram (TEE). However, these techniques are also complicated, time consuming, and expensive. For instance, TEE requires insertion of a flexible tube into a patient's esophagus, while MRI places a patient in an immobile position for prolonged period of time in claustrophobic conditions.

Therefore there is a need for a system and method to measure LV torsion using an imaging technique that is fast, relatively inexpensive and easy to operate.

An aspect of the present disclosure is to provide a system and method for measuring left ventricular torsion angle using three-dimensional ultrasound data. An imaging system collects three-dimensional ultrasound data of at least one cardiac cycle. One or more tracking points are placed on the three-dimensional data at the beginning of the systolic phase. The points are then tracked throughout the systolic phase to determine the torsion angle of the left ventricle.

Another aspect of the present invention is to slice three-dimensional ultrasound data to obtain two-dimensional slices capturing first and second short axis views of the left ventricle, one at the beginning of the systolic phase and another at the end thereof. Thereafter, two or more tracking points are placed on the first short axis view taken at the beginning of the systolic phase and a first line is drawn intersecting the points. The points are tracked on the second short axis view and a second line is drawn which intersects the first line at angle that is the same as the torsion angle.

According to one embodiment of the present disclosure, a system for determining at least one torsion angle of a left ventricle is disclosed. The system includes data acquisition hardware for collecting three-dimensional ultrasound data of the left ventricle to obtain at least one first two-dimensional view and at least one second two-dimensional view thereof, wherein the first two-dimensional view is obtained at the beginning of systolic phase and the second two-dimensional view is obtained at the end of the systolic phase, a display for use in placing at least two tracking points on the at least one first two-dimensional view to draw a first torsion line, and processing means for tracking the at least two tracking points to extrapolate the position thereof on the at least one second two-dimensional view and to draw a second torsion line and calculating the at least one torsion angle by measuring an angle formed by the intersection of the first and second torsion lines.

According to another embodiment of the present disclosure, a method for determining at least one torsion angle of a left ventricle is disclosed. The method includes the steps of collecting three-dimensional ultrasound data of the left ventricle to obtain at least one first two-dimensional view and at least one second two-dimensional view thereof, wherein the first two-dimensional view is obtained at about the beginning of a cardiac phase and the second two-dimensional view is obtained at about the end of the cardiac phase, placing at least two tracking points on the at least one first two-dimensional view to draw a first torsion line, tracking the at least two tracking points to extrapolate the position thereof on the at least one second two-dimensional view and to draw a second torsion line, and calculating the at least one torsion angle by measuring an angle formed by the intersection of the first and second torsion lines.

According to a further embodiment of the present disclosure, a method for determining at least one torsion angle of a left ventricle is disclosed. The method includes the steps of collecting three-dimensional ultrasound data of the left ventricle from about the beginning of a cardiac phase to about the end of the cardiac phase, placing at least four three-dimensional tracking points on the three-dimensional ultrasound data, processing the at least four three-dimensional tracking points to generate a three-dimensional mesh, and calculating the at least one torsion angle by comparing the three-dimensional mesh to the three-dimensional ultrasound data.

According to another embodiment of the present disclosure, a series of programmable instructions stored on a computer-readable medium and being executable by at least one processor for determining at least one torsion angle of a left ventricle is disclosed. The series of programmable instructions includes the steps of collecting three-dimensional ultrasound data of the left ventricle to obtain at least one first two-dimensional view and at least one second two-dimensional view thereof, wherein the first two-dimensional view is obtained at the beginning of systolic phase and the second two-dimensional view is obtained at the end of the systolic phase, placing at least two tracking points on the at least one first two-dimensional view to draw a first torsion line, tracking the at least two tracking points to extrapolate the position thereof on the at least one second two-dimensional view and to draw a second torsion line, and calculating the at least one torsion angle by measuring an angle formed by the intersection of the first and second torsion lines.

Various embodiments of the disclosure will be described herein below with reference to the figures wherein.

The present disclosure relates to system and method for measuring left ventricular torsion. The method includes the step of acquiring three-dimensional (3D) visual data of the left ventricle (LV) using a 3D ultrasound echograph. A two-dimensional cross-sectional view is obtained. More particularly, a short-axis view of the left ventricle is obtained and certain anatomical points are selected for tracking. The anatomical points are tracked for a predetermined cycle to quantify the torsion angles of the LV. Those skilled in the art will appreciate that the present disclosure is described using the human heart as an example and that the disclosure may apply to hearts of other species capable of having LV torsion.

In the present disclosure, torsion angle includes an angle per frame of imaging data capturing the cardiac cycle, which may be represented a curve, maximum torsion angle of the curve, the speed of the torsion (e.g., degrees per second) represented also as a curve, maximum speed of torsion, time when the angle reaches its maximum value (e.g., in degrees or degrees per second), and the like.

Figure 1:
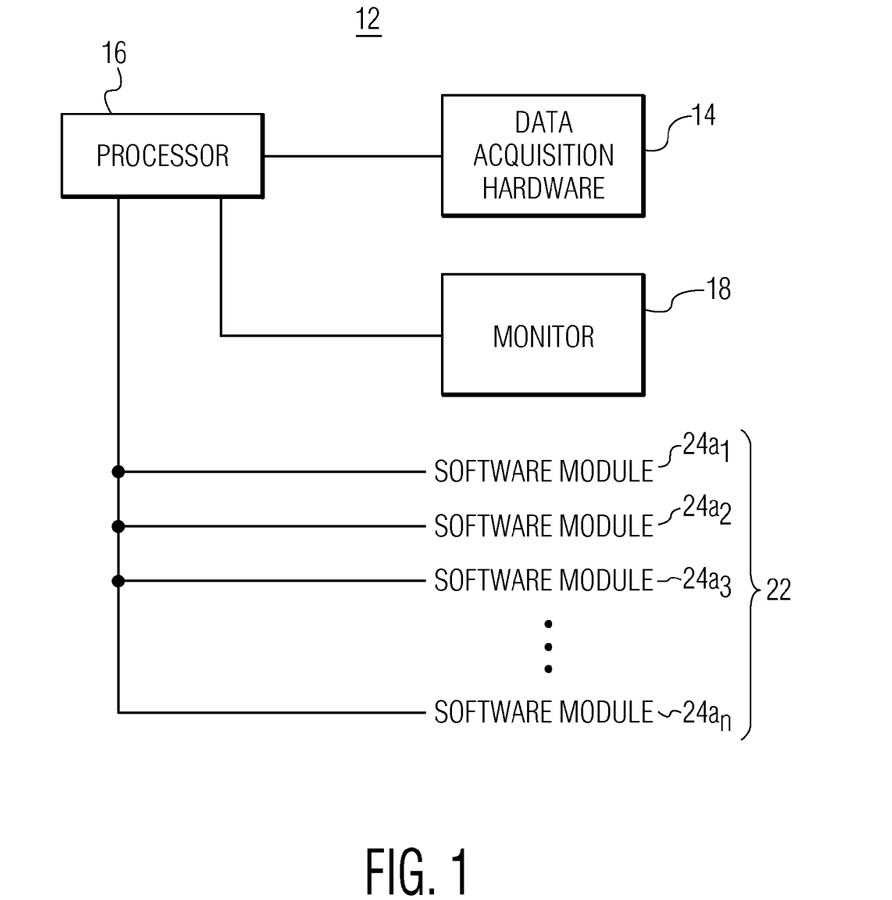
FIG. 1 is a block diagram of the system according to the present disclosure.

With reference to FIG. 1, an ultrasound imaging system 12 is shown. The system 12 is capable of producing 3D ultrasound echographs, such the SONOS™ 7500 digital echocardiography system or iE33 PMS system available from Philips Medical Systems, for acquiring and storing ultrasound images. The system 12 includes data acquisition hardware 14, such as an ultrasonic transducer and a keyboard, a processor 16 for processing the data, and a monitor 18 capable of displaying a graphical user interface of a software quantification tool, the echographs obtained by the imaging system 12 and two-dimensional slices thereof are explained in more detail below.

The system 12 further includes operational software 22 capable of being executed by the processor 16 for performing the various functions of the imaging system 12, such as ultrasound image acquisition and harmonic image enhancement. The operational software 22 includes a plurality of software modules $24a_1$-$24a_n$ or plug-ins for performing the various functions, including the functions and features of the present disclosure.

The plurality of software modules $24a_1$-$24a_n$ are preferably stored within a memory storage device, such as a computer hard drive, within a memory module, such as a RAM or ROM module, and/or on a computer readable medium, such as a CD-ROM, and are capable of being accessed for execution by the processor 16. The plurality of software modules $24a_1$-$24a_n$ are preferably incorporated within the software quantification tool for use in off-line image review, quantification and interpretation of ultrasound images and other related data.

Figure 2:
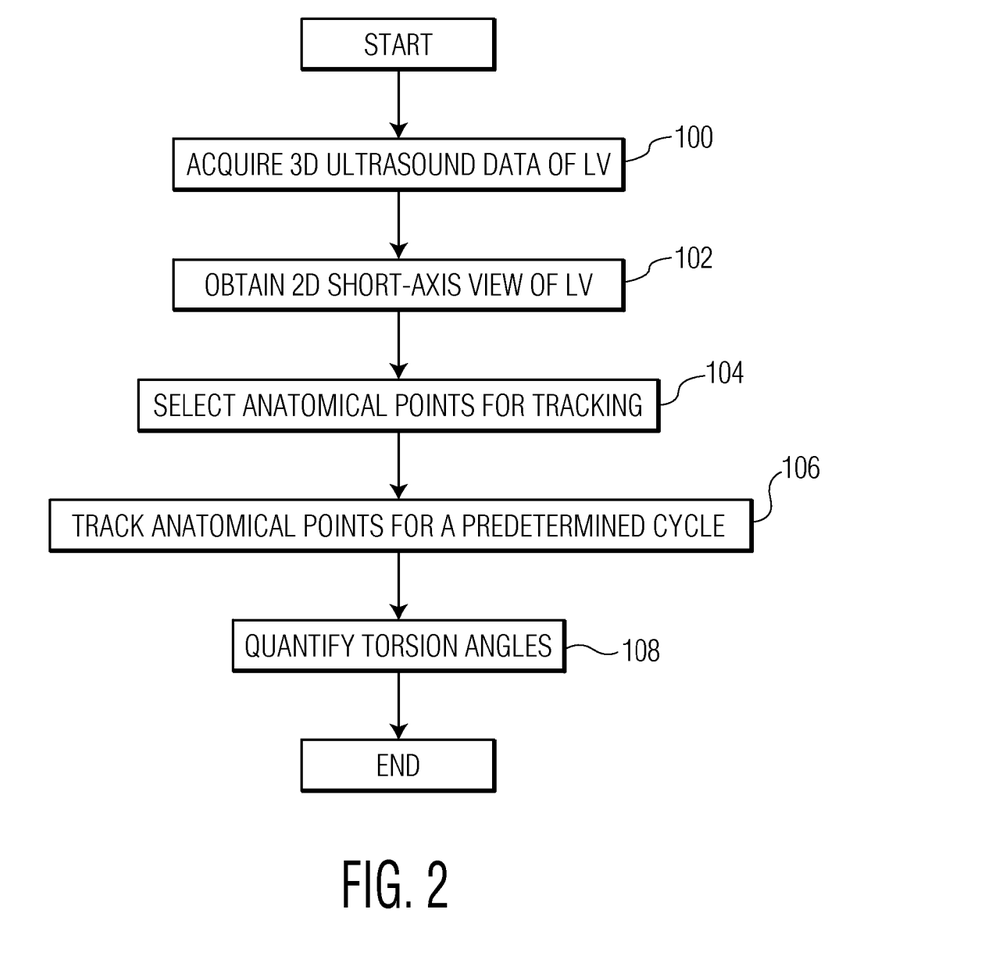
FIG. 2 is an operational flow block diagram illustrating a method of operation according to the present disclosure.

With reference to FIG. 2, the method for quantifying the torsion of the LV will now be discussed. In step 100, a sequence of 3D images of the heart is obtained using the imaging system 12. In embodiments, the sequence of 3D images represents one or more cardiac cycles including systole and diastole phases. The image sequence can be acquired at a rate of about 15 to about 30 or about 50 images per second, each image of the sequence being associated to an instance of the cardiac cycle.

Figure 6:
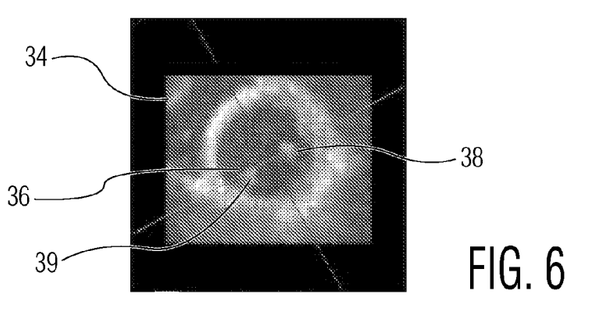
FIG. 6 is a short axis ultrasound image of the heart of FIG. 3 according to the present disclosure.

In step 102, once the 3D ultrasound data is collected, a short axis view of the LV is obtained using one of the software modules 24a. As is known in the art, the heart is described as having a longitudinal and a short axis. The short axis passes laterally through the heart, a slice taken along the short axis represents a cross-sectional view of the heart as shown in FIG. 6 and discussed in more detail below.

Figure 3:
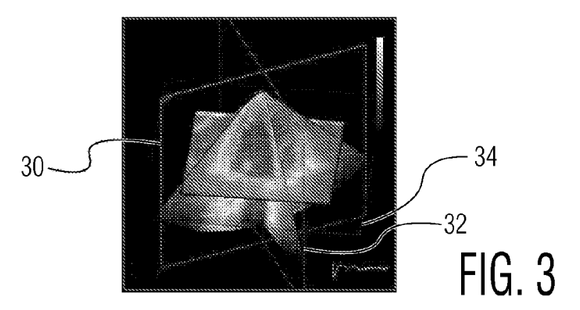
FIG. 3 is three-dimensional ultrasound image of a heart according to the present disclosure.
Figure 4:
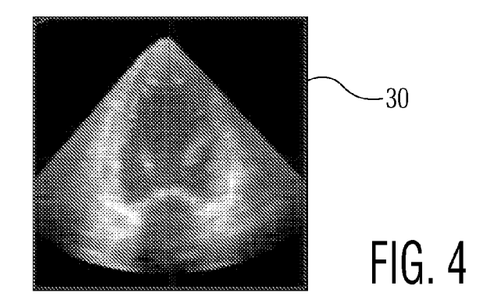
FIG. 4 is a two chamber ultrasound image of the heart of FIG. 3 according to the present disclosure.
Figure 5:
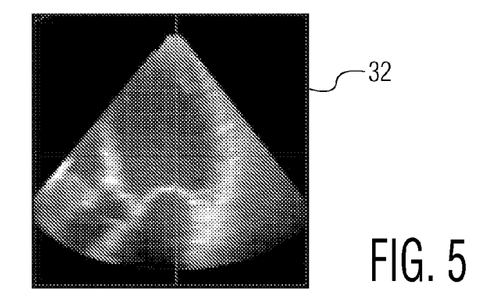
FIG. 5 is a single chamber ultrasound image of the heart of FIG. 3 according to the present disclosure.

FIG. 3 shows a three-dimensional ultrasound image of the heart obtained in step 100 including three two-dimensional slices 30, 32, 34 therethrough. As shown in FIG. 4, the slice 30 is vertical and includes the image of the two-chambers. With reference to FIG. 5, the slice 32 is also vertical and includes a single chamber view of the heart. FIG. 6 shows the lateral slice 34 which includes a short axis view of the heart. The slice 34 is obtained in step 102 using one of the software modules 24a. It is envisioned that one or more lateral slices can be obtained to calculate the torsion angle at each of these views.

The short axis view of the lateral slice 34 represents one view of a left ventricle (LV) 36 showing an anterior papillary muscle 38 and a posterior papillary muscle 39 which will be used as anatomical tracking points in tracking the LV torsion angles as discussed in more detail below. It is envisioned that a plurality of lateral slices can be taken to obtain a plurality of short axis views.

During the cardiac cycle, and more specifically during the systolic phase, the LV 36 is contracting its muscle fibers. Since the cardiac fibers of the LV 36 are oriented in layers, a plurality of contractions are known: longitudinal contraction, where the distance between the valve plane and the apex of the heart is reduced; radial contraction, where the endocardial border is moved inward, toward the center of the heart thereby reducing the size of the chamber of the LV 36; and torsion motion the study of which, more particularly, angle quantification and analysis are the subject of the present disclosure.

Figure 7A:
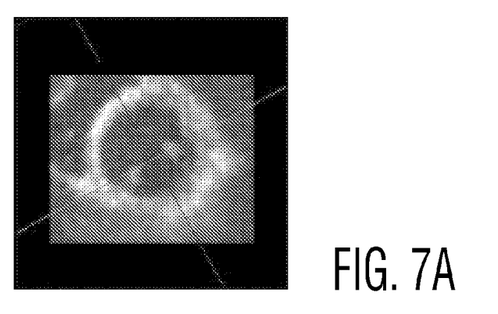
FIGS. 7A-D are short axis ultrasound images showing torsion motion of the heart of FIG. 3 according to the present disclosure.
Figure 7B:
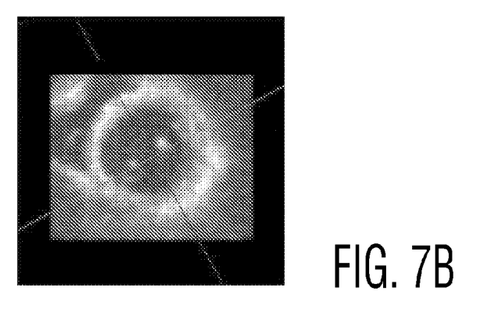
Figure 7C:
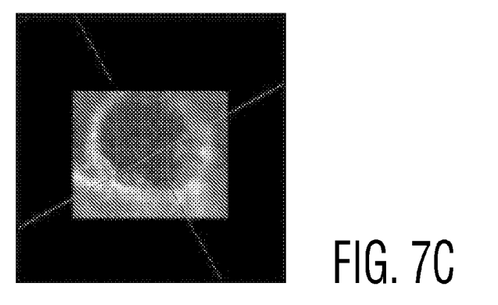
Figure 7D:
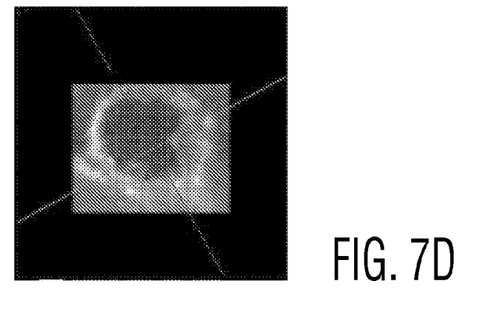

During the torsion motion the apical portion of the LV 36 is rotated counter clockwise as the basal part close to the valve plane is rotated in the opposite, clockwise direction, resulting in the torsion motion as shown in FIGS. 7A-D. Therefore, for accurate calculation of the torsion angles preferably one or more lateral slices of the LV 36 are used. More particularly, FIGS. 7A-D illustrate the rotation of the LV 36 during the systolic phase. FIG. 7A shows a short axis view taken at the papillary muscles 38, 39 slice at the end of the diastolic phase of the cardiac cycle (e.g., beginning of the systolic phase). FIG. 7B shows another short axis view taken at the papillary muscles 38, 39 slice at the end of the systolic phase. FIG. 7C shows a further short axis view of the LV 36 taken closer to the apex and below the papillary muscles 38, 39 at the end of the systolic phase. And FIG. 7D shows a final short axis view of the LV 36 taken at the same slice as FIG. 7D but at the end of the systolic phase.

Figure 8A:
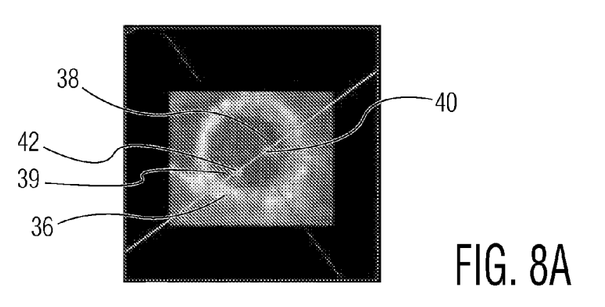
FIGS. 8A-D are short axis ultrasound images showing tracking of papillary muscle tip of the heart of FIG. 3 according to the present disclosure.

After one or more short axis views of the LV 36 is obtained in step 102 as shown in FIGS. 6, 7A-D, in step 104, tracking points are selected. With reference to FIG. 8A, a tracking point 40 is placed on the anterior papillary muscle 38 and a tracking point 42 is placed on the posterior papillary muscle 39. The placement of the tracking points is implemented using one of the software modules 24a. The preferred view is displayed on the monitor 18 and the user selects the tracking points 40, 42 by using a pointer device (not shown) or another input device.

At least two tracking points are preferably used to determine the torsion angle of the LV 36. In addition, the tracking points may be placed near or within other anatomical regions of the LV 36, such as the cardiac muscle, the mitrial valve annulus, and the like. The above placement of tracking points is merely an illustrative embodiment of the present disclosure. It is envisioned that the entire cardiac muscle may be tracked (e.g., by using mesh overlay analysis).

The placement of tracking points 40, 42 is accomplished on the short axis view of the slice taken at the anterior papillary muscles 38, 39 at the end of the diastolic phase as shown in FIG. 8A, which shows the same cross-sectional view as FIG. 7A, namely of the slice taken at the anterior papillary muscles 38, 39 at the end of the diastolic phase. This view best represents the beginning of the systolic phase during which torsion motion can be detected. In addition, this slice also provides one view of the papillary muscles 38, 39, which are useful as anatomical markers.

It is envisioned that tracking points can be placed on multiple lateral views obtained from multiple slices of the LV 36. More specifically, with reference to FIGS. 7C-D a lateral slice of the LV 36 is shown that is closer to the apex of the heart, which can also be used to place tracking points thereon and obtain torsion angle measurements. Collecting multiple measurements of torsion angles at different portions of the LV 36 allows for better analysis than simply comparing a single measurement obtained from one lateral view.

In step 106, the tracking points 40, 42 are tracked by the system 12 to determine the torsion angle during the systolic phase. The tracking is accomplished by referencing the position of the tracking points 40, 42 at the end of the systolic phase as shown in FIG. 8C with the position of the tracking points 40, 42 at the end of the diastole phase shown in FIG. 8A.

Figure 8B:
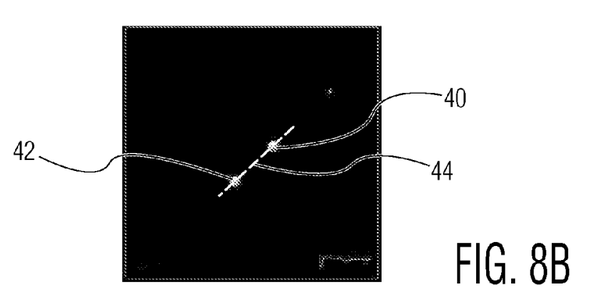
Figure 8C:
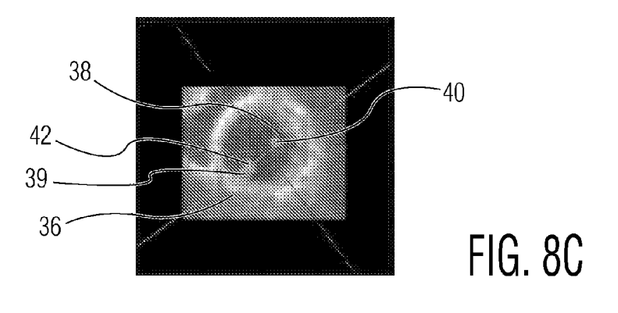

More particularly, FIG. 8C shows a substantially similar view to the one shown in FIG. 7C. FIG. 8C shows the tracking points 40, 42 placed at the papillary muscles 38, 39 at the end of the systolic phase at the same lateral slice as the one shown in FIG. 8A. At the end of the systolic phase, the papillary muscles have shifted from their original position at the end of the diastolic phase as shown in FIG. 8A. The system 12 determines the shift of the tracking points 40, 42, and more specifically measures the angle of the shift which is the same as the torsion angle of the LV 36.

Figure 8D:
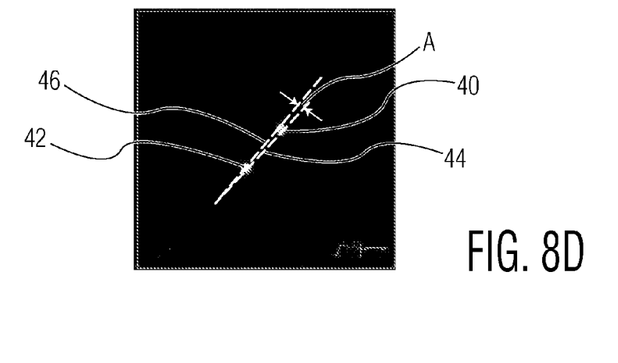

FIG. 8B shows the tracking points 40, 42 as they are positioned at the end of the diastolic phase and FIG. 8D shows the tracking points 40, 42 as they are positioned at the end of the systolic phase. The system 12 extrapolates a first torsion line 44, more specifically, the first line 44 is drawn intersecting the tracking points 40, 42 after the tracking points 40, 42 are placed as shown in FIG. 8A.

The system 12 thereafter generates a second torsion line 46 which intersects the tracking points 40, 42 as they are positioned at the end of the systolic phase. The first and second lines 44 and 46 intersect each other at an angle A. The system 12 determines the angle A in step 108. The angle A is the same as the torsion angle of the LV 36 and allows for determination whether the torsion angle is within norm.

The tracking step is repeated for all tracking points located on all lateral slices, if more than one slice is used. If multiple slices are utilized, then for each slice used, at least two images are obtained, one image of the LV 36 at the beginning of the systolic phase and another at the end of the systolic phase. As discussed above with reference to FIGS. 8A-D having the images of a given slice at the beginning and the end of the systolic phase allows for extrapolation of the first and second torsion lines.

Figure 9:
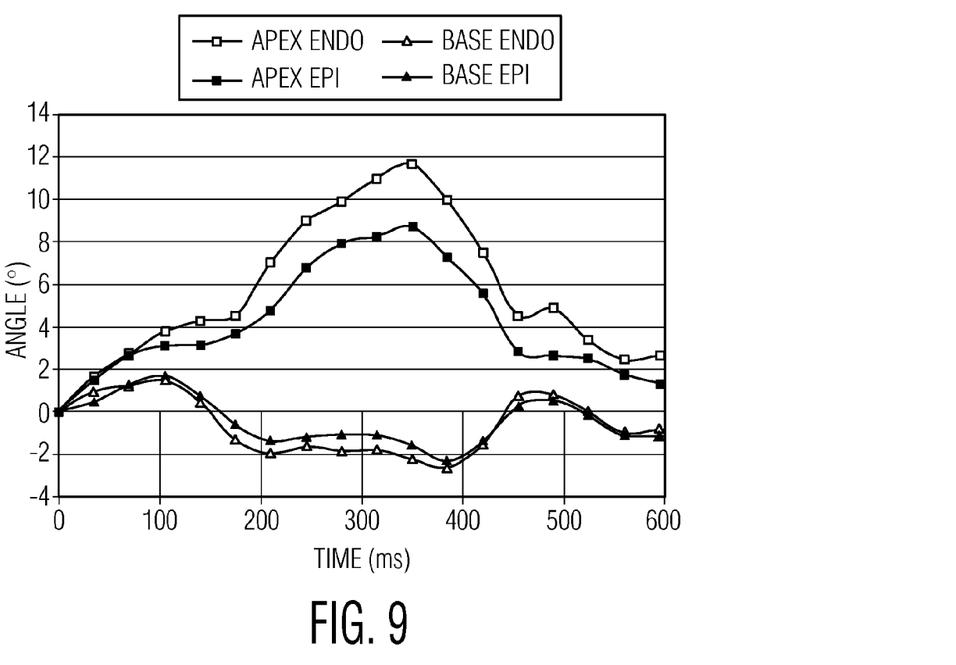
FIG. 9 a graph illustrating normal rotation angles of the left ventricle of the heart of FIG. 3 according to the present disclosure.

The system 12 may include data on the normal torsion angles or an outside source containing the same data may be referenced in determining whether the angle A is normal. FIG. 9 shows a graph illustrating normal torsion angles of the LV 36 during a cardiac cycle at apical and basal slices for both endocardial and epicardial borders. Comparing the angle A to the data in FIG. 9 the operator of the system 12 can analyze or the system 12 can analyze the data using one of the software modules 24a to determine whether the angle A is normal.

It is also envisioned that other parameters can be extracted in step 108. The system 12 may calculate the global torsion angle, which describes the torsion of the entire LV 36, regional torsion angle, which describes the torsion for a particular segment of the LV 36. The regional torsion angle is particularly useful as LV 36 is conventionally subdivided into seventeen anatomical regions during analysis of cardiac images (e.g., from valve to apex). More particularly, regional torsion angles can be compares with each other. The system 12 may compute the regional torsion angle for each of the seventeen segments. In addition, the system 12 may calculate local torsion angles, which are parametric representation of the torsion angle. The local torsion angles are computed and displayed onto a 3D mesh (e.g., overlaid onto 3D data) or onto a 2D representation (e.g., a polar map, "Bull's Eye" plot, etc.).

Figure 10:
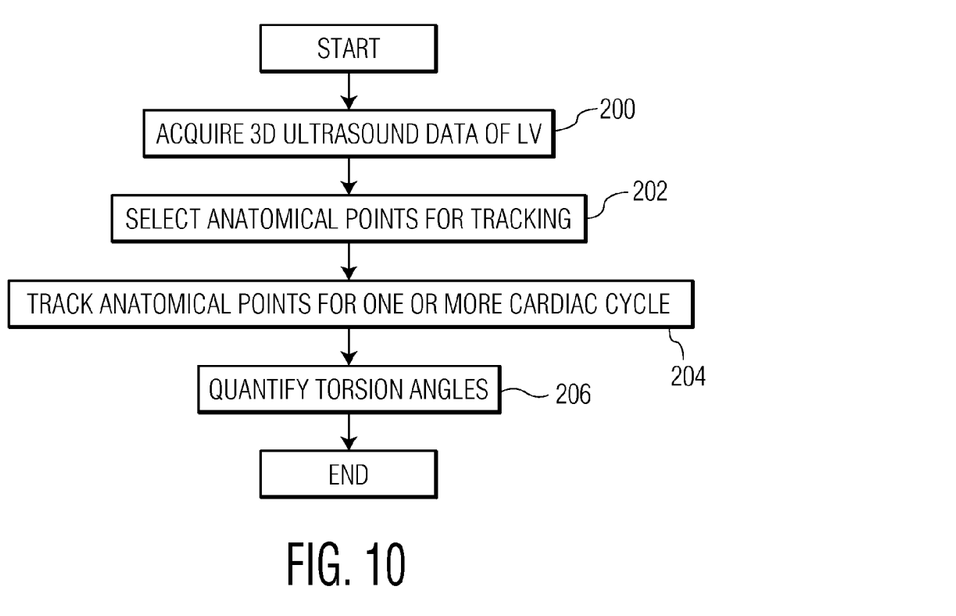
FIG. 10 is an operational flow block diagram illustrating an alternate method of operation according to the present disclosure.
Figure 11:
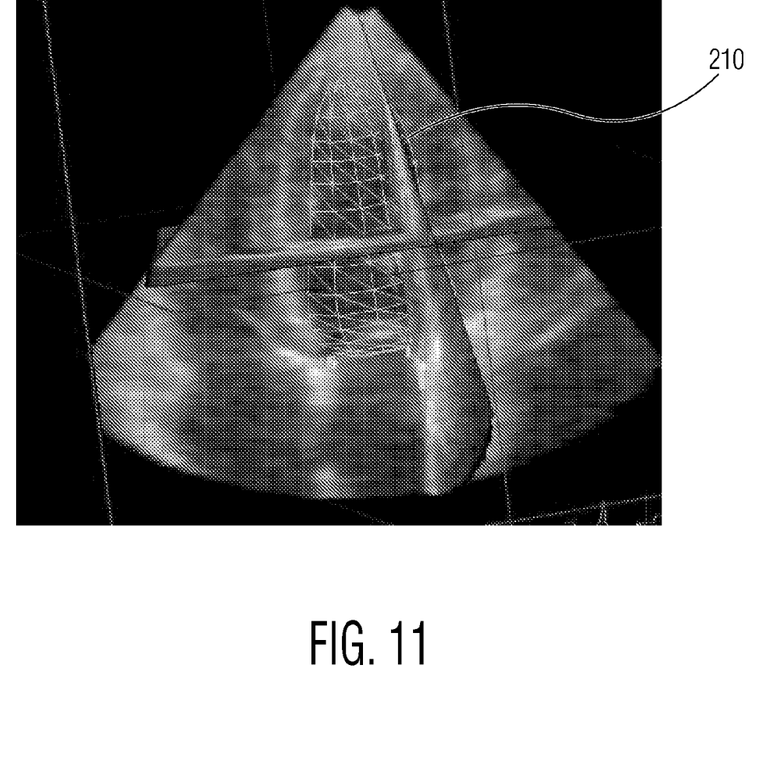
FIG. 11 is a three-dimensional ultrasound image of a heart having a three-dimensional mesh according to the present disclosure.

FIG. 10 shows an alternate method for calculating LV torsion angles. In step 200 a sequence of 3D images of the heart, including one or more cardiac cycles, is obtained using the imaging system 12. A sample 3D cardiac cycle data is shown in FIG. 11. Unlike in method shown in FIG. 2 and discussed above, the 3D data is not sliced to obtain 2D short-axis views of the LV 36. Instead, the user in step 202 enters four or five 3D tracking points in the 3D data, more specifically, three or four points are placed at the mitrial valve level and one is placed at the endocardial apex. In embodiments, the points may be selected automatically or semi-automatically with the aid of the system 12 (e.g., the user selects initial five points, while the system 12 finishes selecting the rest or the points). It is also envisioned that the three-dimensional tracking points may be placed using two-dimensional slices and then extrapolated into three-dimensional data.

In step 204, the tracking points are tracked. More particularly, the imaging system 12 determines affine deformation between the average shape of the LV 36 which includes the four or five tracking points as represented by a 3D mesh 210 and the tracking points. An automatic deformation procedure is also performed to the average shape to match to the 3D data (e.g., a 3D "snake-like" approach, which is within the purview of those skilled in the art). Tracking may be accomplished using dense motion field calculations which are computed at all locations of the 3D data. Placement of tracking points and processing thereof can be accomplished using Philips QLab image processing software, and more specifically the 3DQAdvanced plug-in, both available from Philips Medical Systems, N.A., 22100 Bothell Everett Highway, P.O. Box 3003, Bothell, Wash. 98041-3003. In step, 206 the system 12 quantifies torsion angles in substantially similar manner as the method of FIG. 2.

What has been described herein is merely illustrative of the principles of the present disclosure. For example, the system and method described above and implemented as the best mode for operating the present disclosure are for illustration purposes only. Other arrangements and methods may be implemented by those skilled in the art without departing from the scope and spirit of this disclosure.

The invention claimed is:

1. A method for determining at least one torsion angle of a left ventricle comprising the steps of:
    collecting three-dimensional ultrasound data of the left ventricle with an ultrasonic imaging system at two points in time during a cardiac cycle to obtain a two-dimensional longitudinal axis view and at least one first short axis two-dimensional view of an anatomical landmark of the heart at a first cardiac phase and a two-dimensional longitudinal axis view and at least one second short-axis two-dimensional view of the anatomical landmark of the heart at a second cardiac phase, wherein the first cardiac phase is at about the beginning of the systolic cardiac phase and the second cardiac phase is at about the end of the systolic cardiac phase;

placing at least two tracking points on the anatomical landmark of the first short axis two-dimensional view to draw a first torsion line connecting the tracking points;

tracking the at least two tracking points to positions on the anatomical landmark of the second short axis two-dimensional view to draw a second torsion line connecting the tracking points; and calculating the at least one torsion angle by measuring an angle formed by the intersection of the first and second torsion lines.

2. A method as in claim 1, wherein the at least two tracking points are placed in proximity of an anatomical landmark of the left ventricle.

3. A method as in claim 2, wherein the anatomical landmark is selected from the group consisting of papillary muscles, mitrial valve annulus, and cardiac muscle.

4. A method as in claim 1, the method further comprising:
comparing the at least one torsion angle with normalized torsion angle data.

5. A method as in claim 1, wherein the cardiac phase is a systolic phase.

6. A method as in claim 1, wherein the at least one first two-dimensional view is a short axis view of the left ventricle.

7. A method as in claim 6, wherein the short axis view of the left ventricle is a slice taken through papillary muscle.

8. A method as in claim 1, wherein the at least one second two-dimensional view is a short axis view of the left ventricle.

9. A method as in claim 8, wherein the short axis view of the left ventricle is a slice taken through papillary muscles.

10. The method of claim 1, wherein collecting three-dimensional ultrasound data at the first cardiac phase further comprises obtaining a third short axis two-dimensional view taken closer to the apex and below the papillary muscle; and
wherein collecting three-dimensional ultrasound data at the second cardiac phase further comprises obtaining a fourth short axis two-dimensional view taken of the same slice as the third short axis view.

11. The method of claim 10, further comprising:
placing at least two tracking points on the cardiac muscle of the third short axis two-dimensional view to draw a third torsion line connecting the tracking points;
tracking the at least two tracking points of the third short axis two-dimensional view to positions on the cardiac muscle of the fourth short axis two-dimensional view to draw a fourth torsion line connecting the tracking points; and
calculating the at least one torsion angle by measuring an angle formed by the intersection of the third and fourth torsion lines.

12. An ultrasound imaging system for determining at least one torsion angle of a left ventricle comprising:
data acquisition hardware for collecting three-dimensional ultrasound data of the left ventricle at two points in time during a cardiac cycle to obtain a two-dimensional longitudinal axis view and at least one first short axis two-dimensional view of an anatomical landmark of the heart at a first cardiac phase and a two-dimensional longitudinal axis view and at least one second short axis two-dimensional view of the anatomical landmark at a second cardiac phase,
wherein the first cardiac phase is at the beginning of a systolic phase and the second cardiac phase is at about the end of the systolic phase;
a display for use in for placing at least two tracking points on the anatomical landmark of the first short axis two-dimensional view to draw a first torsion line; and
a processor for tracking the at least two tracking points to positions thereof on the anatomical landmark of the second short axis two-dimensional view to draw a second torsion line and calculating the at least one torsion angle by measuring an angle formed by the intersection of the first and second torsion lines.

13. A system as in claim 12, wherein the at least two tracking points are placed in proximity of an anatomical landmark of the left ventricle.

14. A system as in claim 13, wherein the anatomical landmark is selected from the group consisting of papillary muscles, mitrial valve annulus, and cardiac muscle.

15. A system as in claim 12, wherein the processor compares the at least one torsion angle with normalized torsion angle data.

16. A system as in claim 12, wherein the cardiac phase is a systolic phase.

17. A system as in claim 12, wherein the at least one first two-dimensional view is a short axis view of the left ventricle.

18. A system as in claim 17, wherein the short axis view of the left ventricle is a slice taken through papillary muscles.

19. A system as in claim 12, wherein the at least one second two-dimensional view is a short axis view of the left ventricle.

20. A system as in claim 19, wherein the short axis view of the left ventricle is a slice taken through papillary muscles.

21. A system as in claim 12, wherein the data acquisition hardware is further adapted for collecting three-dimensional ultrasound data at the first cardiac phase which comprises obtaining a third short axis two-dimensional view taken closer to the apex and below the papillary muscle; and
wherein the data acquisition hardware is further adapted for collecting three-dimensional ultrasound data at the second cardiac phase which comprises obtaining a fourth short axis two-dimensional view taken of the same slice as the third short axis view.

22. A system as in claim 21, wherein the display is further adapted for use in placing at least two tracking points on the cardiac muscle of the third short axis two-dimensional view to draw a third torsion line connecting the tracking points; and
wherein the processing means is further adapted for tracking the at least two tracking points of the third short axis two-dimensional view to positions on the cardiac muscle of the fourth short axis two-dimensional view to draw a fourth torsion line connecting the tracking points; and calculating at least one torsion angle by measuring an angle formed by the intersection of the third and fourth torsion lines.

* * * * *